United States Patent [19]

Skarlos

[11] 4,357,667
[45] Nov. 2, 1982

[54] ON-LINE OIL-IN-WAX MONITORING APPARATUS AND METHOD

[75] Inventor: Leonidas Skarlos, Beaumont, Tex.

[73] Assignee: Texaco Inc., White Plains, N.Y.

[21] Appl. No.: 190,123

[22] Filed: Sep. 24, 1980

[51] Int. Cl.³ ............................................. G01N 11/00
[52] U.S. Cl. .................................... 364/496; 364/500; 73/61 R; 196/14.5
[58] Field of Search .......................... 73/61 R, 64, 53; 324/300; 364/496, 500, 497, 501, 552; 208/28, 31, DIG. 1; 196/14.5

[56] References Cited

U.S. PATENT DOCUMENTS

| | | | |
|---|---|---|---|
| 3,549,514 | 12/1970 | Brown et al. | 364/500 X |
| 3,718,809 | 2/1973 | Woodle | 364/500 |
| 3,720,599 | 3/1973 | Gould | 196/14.5 X |
| 3,777,127 | 12/1973 | Goetchius et al. | 364/497 |
| 3,925,721 | 12/1975 | Petroff | 324/200 |
| 3,965,723 | 6/1976 | Harrison et al. | 73/61 R X |
| 3,972,779 | 8/1976 | Harrison | 364/500 X |
| 3,982,422 | 9/1976 | Harrison et al. | 73/61 R X |
| 4,053,744 | 10/1977 | Woodle | 364/501 |
| 4,260,580 | 4/1981 | Sindo et al. | 364/497 X |
| 4,266,425 | 5/1981 | Allport | 73/61 R |

Primary Examiner—Edward J. Wise
Attorney, Agent, or Firm—Carl G. Ries; Robert A. Kulason; Ronald G. Gillespie

[57] ABSTRACT

An on-line oil-in-wax monitor includes a sampling device which samples a stream of a liquid wax and oil mixture periodically to provide samples. The wax in each sample is solidified. Sensing apparatus senses the oil in each sample and provides a corresponding sensed oil signal. The oil content of the stream is then indicated in accordance with the sensed oil signal.

7 Claims, 5 Drawing Figures

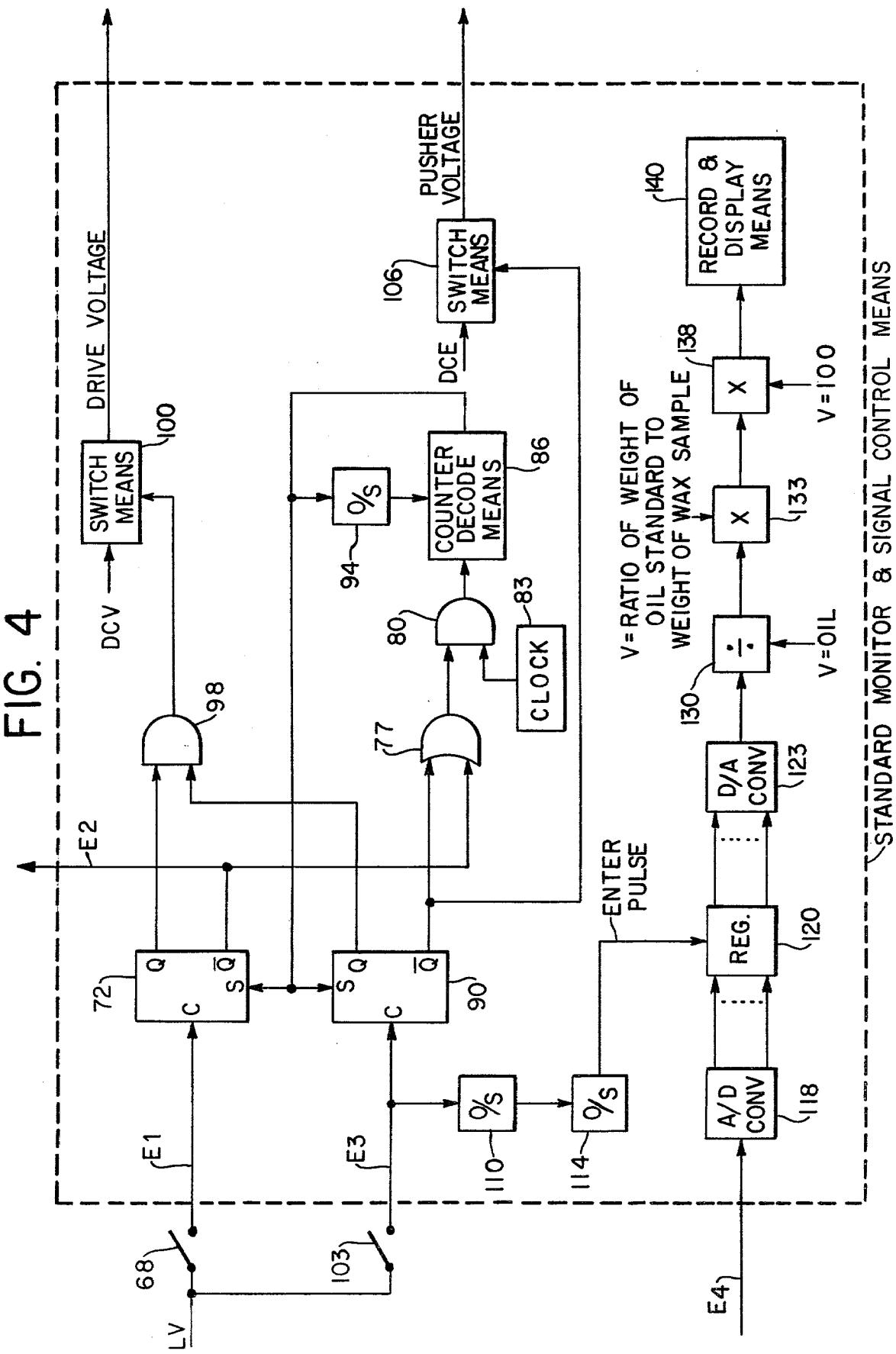

ON-LINE OIL-IN-WAX MONITORING APPARATUS AND METHOD

BACKGROUND OF THE INVENTION

FIELD OF THE INVENTION

The present invention relates to monitoring apparatus and methods in general and, more particularly, monitoring apparatus and methods for use in a petroleum refinery.

SUMMARY OF THE INVENTION

An on-line oil-in-wax monitor includes apparatus for sampling a stream of liquid wax and oil periodically. Chilling apparatus causes the wax in each sample to solidify. A sensor senses the oil in each sample and provides a sensed oil signal corresponding thereto. The oil content of the stream is indicated by a device in accordance with the sensed oil signal.

The objects and advantages of the invention will appear more fully hereinafter from a consideration of the detailed description which follows, taken together with the accompanying drawings wherein two embodiments of the invention are illustrated by way of example. It is to be expressly understood, however, that the drawings are for illustration purposes only and are not be construed as defining the limits of the invention.

DESCRIPTION OF THE DRAWINGS

FIG. 4 is a detailed block diagram of the monitor and control means shown in FIG. 1.

DESCRIPTION OF THE INVENTION

The present invention may be used for the ripid determination of the oil content of waxes in a solvent dewaxing unit. Heretofore the determination of the oil content of wax by ASTM method D-721 or D-3235 took several hours. The present invention when used on-line gives accurate results in minutes.

The following equation is used to determine the oil content of wax:

$$\% \text{ Weight Oil} = (SW/SO)(WO/WW)100,$$

where SW is a signal from a sensor corresponding to the oil in a wax sample, SO is a signal corresponding to an oil standard, WO is the weight of the oil standard, and WW is the weight of a wax sample.

Figure 1:
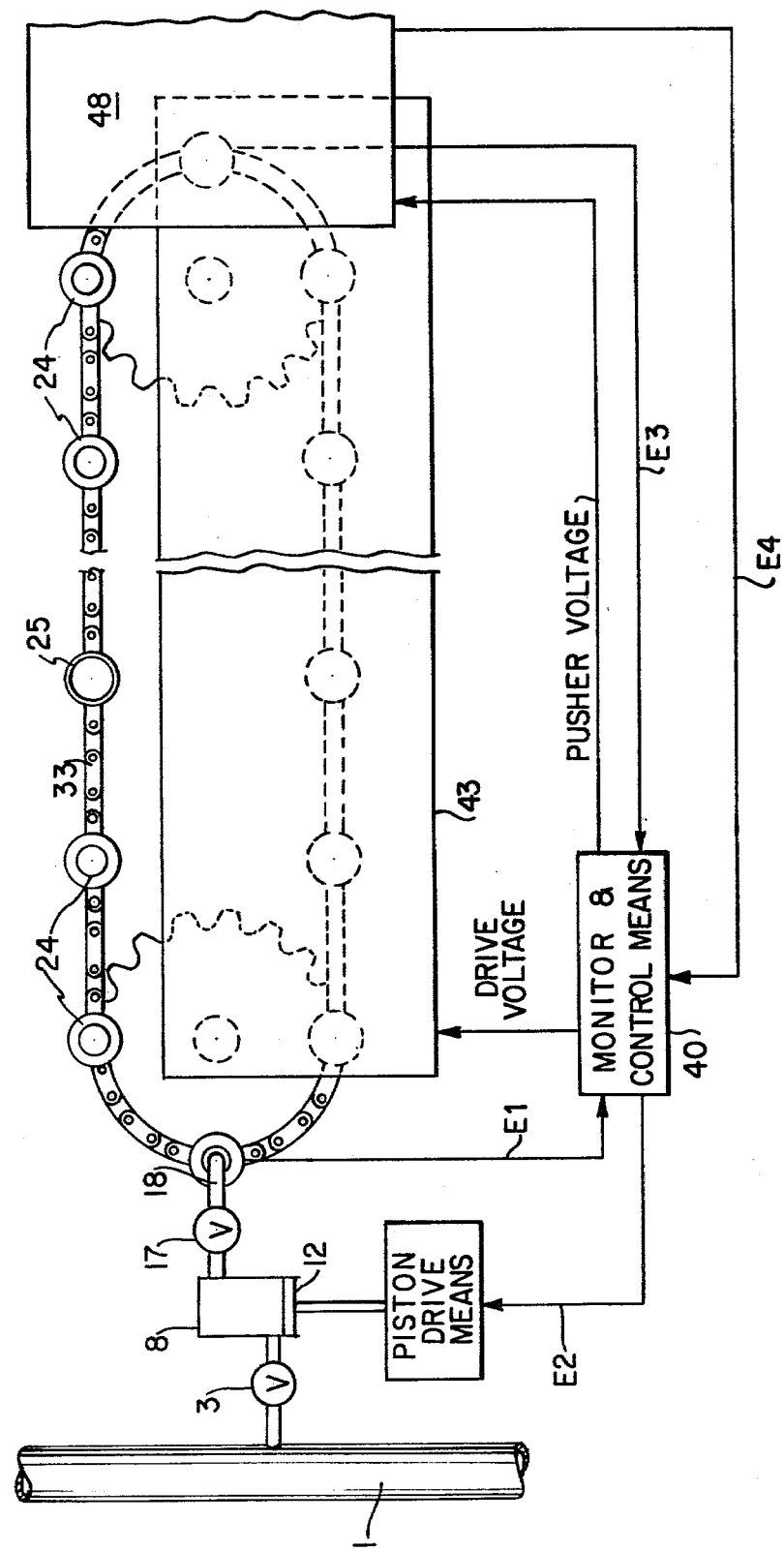
FIG. 1 is a top view of an on line oil in wax monitor, constructed in accordance with the present invention, shown in simplified mechanical form and simplified block diagram form.

Referring now to FIG. 1, liquid wax, which may have oil within it, is flowing in a line 1 and fills a chamber 8 corresponding to a predetermined quantity of the liquid wax, chamber 8 is evacuated by the operation of a piston 12 driven by piston drive means 15. As piston 12 drives to the bottom of chamber 8, the liquid wax builds up sufficient pressure to pass through a check valve 17 to be dispensed by a nozzle 18. Positioned below nozzle 18 is an empty bottle 24, which fits on a bottle pan 25 mounted on an endless conveyor belt 33.

The details of the belt drive mechanism will be discussed hereinafter.

Sufficient to say at this time that as the bottle passes underneath nozzle 18, a microswitch, not shown in FIG. 1, provides a signal El to monitor and control means 40 which provides the drive voltage for the movement of the conveyor belt 33 causing means 40 to cease providing the drive voltage so that the belt stops for a predetermined time, as hereinafter explained, with the empty bottle positioned under nozzle 18. Monitor and control means 40 provides signal E2 to the piston drive means 15 to activate the piston to load the bottle with liquid wax.

Upon completion of the bottle loading time period, the conveyor belt again is operated until another stop time period is encountered which will be described hereinafter. Over a longer period of time the full bottle of liquid wax will pass through a refrigeration unit 43 which cools the wax in the bottles to the point of solidification while the oil still remains as liquid. In time the bottle will pass into sensing means 48 so that when a bottle arrives in a proper position for test in sensing means 48 a microswitch, not shown, provides a signal E3 to monitor and control means 40 which again stops the movement of the conveyor belt as hereinafter explained for purposes of testing the wax samples. Sensing means 48 utilizes low resolution nuclear magnetic resonance to sense the wax content of a bottle 24. The low resolution nuclear magnetic is affected by hydrogen associated with liquids, such as oil, but is not affected by hydrogen associated with solids, such as wax. Sensing means 48 may include a Newport Analyzer Mark 3, manufactured by Newport Oxford Industries, or its equivalent.

Figure 2:
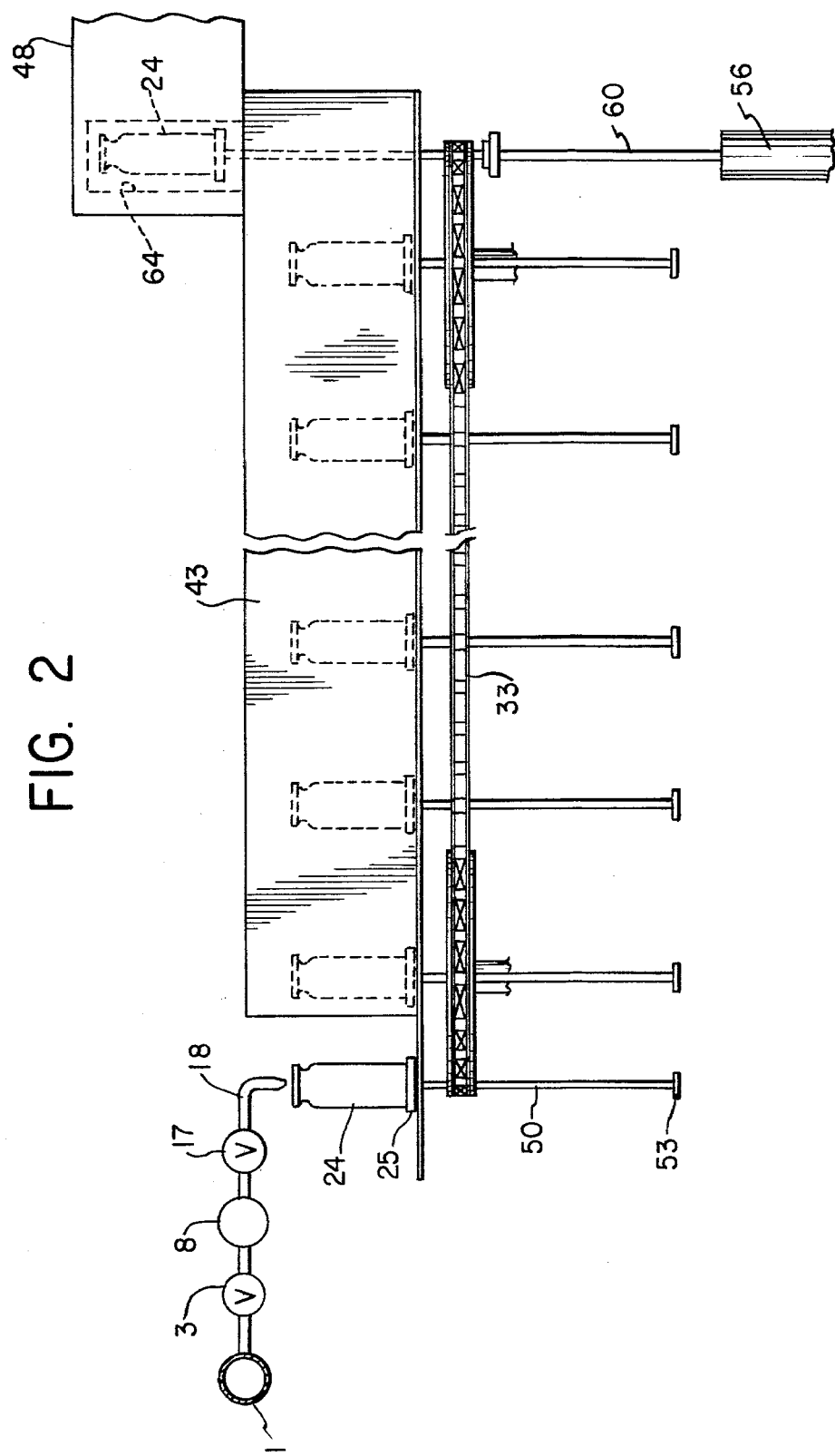
FIG. 2 is a simplified diagram of a side view of the mechanical portion of the on line oil in wax monitor.
Figure 3:
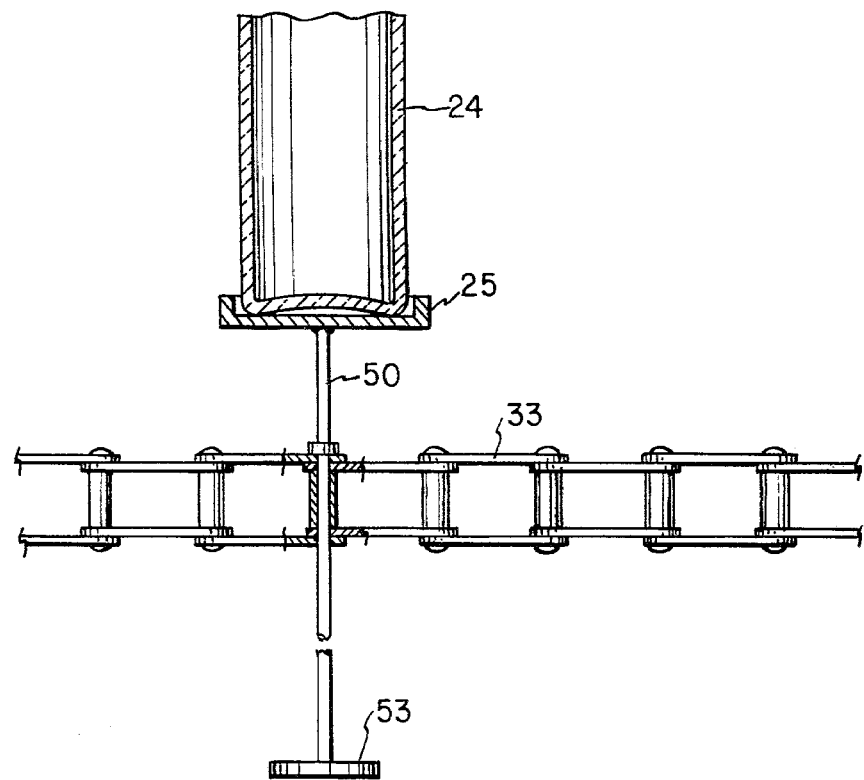
FIG. 3 is a detailed view of a mechanical arrangement of the bottle seat holder shown in FIGS. 1 and 2.

Referring now to FIGS. 2 and 3, each bottle pan 25 is attached to a pusher rod 50 having a pusher head 53 at the opposite end. Rod 50 passes through a hollow link of belt 33. When a bottle 24 filled with wax is in position for test, monitor and control means 40 provides a pusher voltage to a solenoid means 56 causing it to extend a plunger 60 in the direction of pusher rod 50 which in turn elevates bottle 24 into a test chamber 64 of sensing means 48. Sensing means 48 provides a signal E4 corresponding to the ingredients in the test chamber.

Referring now to FIG. 4, the microswitch associated with the filling of the bottles is now assigned the number 68 and receives a negative logic voltage LV so that when activated by the positioning of a bottle 24 beneath nozzle 18, switch 68 closes causing voltage LV to trigger a flip-flop 72 to a clear state. A flip-flop of the type used in the present invention has a set input S and a clear input C, a Q output and a $\overline{Q}$ output, and operates such that while in the set state the Q and $\overline{Q}$ outputs provide a high logic level and a low logic level set level signal, respectively, and while in the clear state the Q and $\overline{Q}$ outputs provide a low logic level and a high logic level signal, respectively. Thus, while in the clear state flip-flop 72 provides the $\overline{Q}$ output signal as signal E2 to commence the dispensing operation and also provides the $\overline{Q}$ output signal through an OR Gate 77 to enable an AND Gate 80. AND Gate 80, when enabled, passes timing pulses from a clock 83 to a counter decode means 86. Counter decode means 86 provides a pulse output after a predetermined time has elapsed in response to the counting of the passed timing pulses from AND Gate 80. The pulse from counter decode means 86 is provided to the set inputs of flip-flops 72, 90 and to a one shot multivibrator 94. The pulse from counter decode means 86 triggers flip-flop 72 back to the set state causing the signal appearing at the $\overline{Q}$ output to go to a low logic level thereby disabling AND Gate 80 to prevent further counting by counter decode means 86.

Flip-flop 72 when triggered to the clear state provides the signal from its Q output at a low logic level to disable an AND Gate 98. Disabled AND Gate 98 provides a low logic level signal to switch means 100 which receives a DC voltage DCV. Switch means 100 is an electronic type single pole, single throw switch which is rendered conductive by a high logic level signal from AND Gate 98 and non-conductive by a low logic level signal from AND Gate 98 to pass or block voltage DCV. Switch means 100 when rendered conductive provides voltage DCV as the drive voltage to the conveyor belt system means. Thus, when AND Gate 98 was disabled, switch means 100 was rendered non-conductive causing it to block voltage DCV so that the conveyor belt 33 stopped.

With the occurrence of the pulse from counter decode means 86, counter decode means 86 was reset by a reset pulse from one-shot 94. Further, with flip-flop 72 providing a high logic level signal at its Q output, switch 100 provided voltage DCV as the drive voltage so that the conveyor belt 33 started to move again.

When the next bottle 24 filled with wax appears in position for testing, the microswitch associated with sensing means 48, which we will now assign the number 103, is closed causing it to pass the logic voltage LV thereby triggering flip-flop 90 to a clear state. The Q and $\overline{Q}$ outputs of flip-flop 90 are connected to AND Gate 98 and OR Gate 77, respectively, so that the operation of conveyor belt 33 as herein before described for the stopping and starting of conveyor belt 33 for the dispensing operation repeats itself and need not be explained again.

The $\overline{Q}$ output of flip-flop 90 is also connected to a single pole, single throw electronic switch means receiving a DC voltage DCE which, when switch 106 is rendered conductive will provide the pusher voltage to operate the solenoid 56 and plunger 60 to elevate a bottle 24 into test chamber 64. Thus, with flip-flop 90 triggered to the clear state, the $\overline{Q}$ output of flip-flop 90 provides a high logic level signal to switch means 106 causing it to pass voltage DCE as the pusher voltage resulting in a bottle 24 being placed in the test chamber. Upon the completion of the predetermined time period by counter decode means 86, flip-flop 90 as herein before explained is triggered to a set state causing the signal appearing at the $\overline{Q}$ output to go to a low logic level thereby rendering the switch means 106 non-conductive causing plunger 60 to then return to a lower level thereby removing bottle 24 from test chamber 64 and in effect placing it again in conveyor belt 33.

It should be noted that in one mode of operation, sensing means 48 is providing signal E4 corresponding to whatever is within test chamber 64. However, since there are many times when there is nothing in the test chamber or that a bottle 24 of wax is in the process of entering or leaving the test chamber, signal E2 at those times is meaningless. Thus, the only valid test data occurs at a time when a bottle 24 is in the test chamber for a sufficient time period to allow the signal E4 to stabilize and properly correspond to the contents of bottle 24.

To assure that only a valid signal E4 is used to determine the oil content of the wax, signal E3 from switch means 103 triggers a one shot multivibrator 110, which acts as a time delay to provide a pulse. The trailing edge of the pulse from one shot 110 triggers another one shot multivibrator 114 to provide an 'enter' pulse.

Signal E4 is provided to an analog-to-digital converter 118 which provides corresponding digital signals to a register 120. Register 120 only enters the digital signals from analog-to-digital converter 118 in response to an 'enter' pulse. Register 120 provides digital signals, corresponding to its contents, to a digital-to-analog converter 123. Digital-to-analog converter 123 provides an analog signal corresponding to a valid measurement of the contents of bottle 24 to a divider 130 which receives a DC voltage corresponding to a signal representative of an oil standard sample. The value for the voltage V being applied to divider 130 may be determined prior to testing by placing a bottle 24 in the sample chamber filled with the oil of the type that would be contained in the wax. An output signal from divider 130 is provided to a multiplier 133 where it is multiplied with the DC voltage corresponding to the ratio of the weight of the oil standard to the weight of the wax sample. Again this voltage may be determined prior to the testing operations although it could just as easily be done as part of a calibration circuitry for the present invention if it is so desired. The output for multiplier 133 is provided to another multiplier 138 where it is multiplied with a direct current voltage corresponding to a value of 100. The output signal provided by multiplier 138 corresponds to the percent weight of oil in the wax in accordance with the foregoing equation. The signal from multiplier 138 is recorded and may be displayed by record and display means 140.

Although the present invention has been described as using the foregoing equation, the equation itself is not necessary. An alternative method would be to establish different percent weights of oil in wax mixtures and obtaining corresponding signals. The signals so obtained are stored and utilized as reference signals. Signal S from digital-to-analog converter 123 is then compared with the reference signals and an appropriate reference signal selected, in accordance with the comparison, for recording and display.

Figure 5:
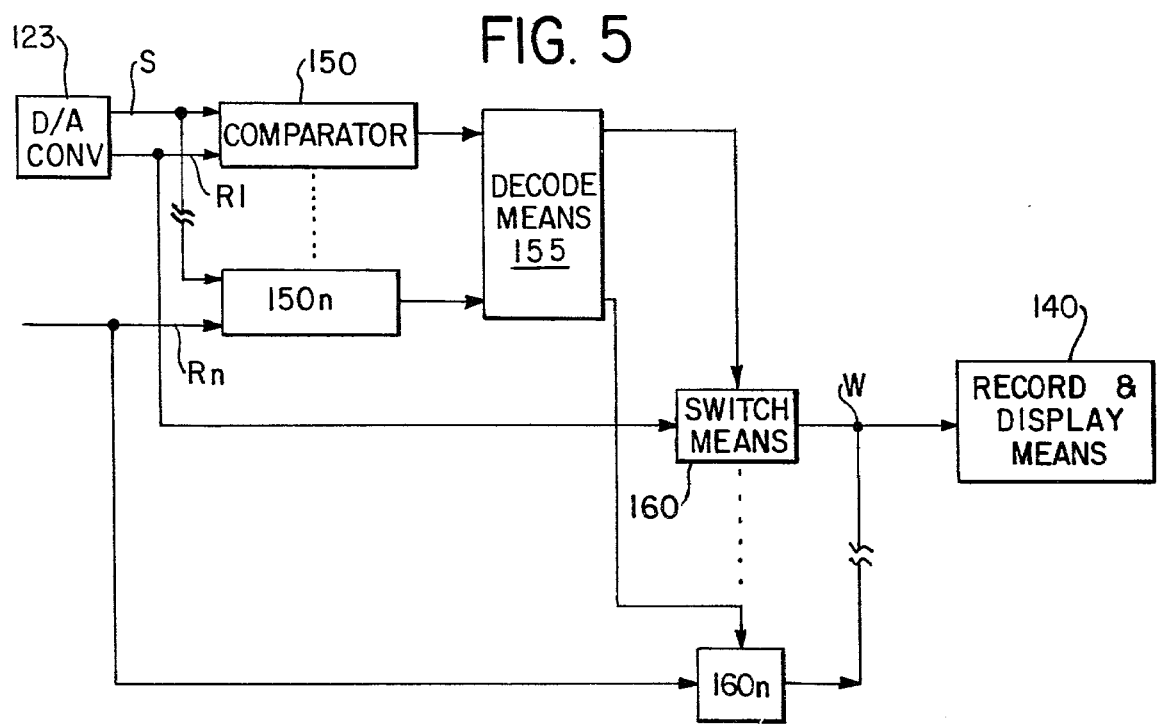
FIG. 5 is a detailed block diagram of a portion of the monitor and control means shown in FIG. 1 for another embodiment of the present invention.

This may be accomplished as shown in FIG. 5, where signal S from digital-to-analog converter 123 is provided to a plurality of comparators 150 through 150n. The break in the line carry signal S indicates any number of comparators may be utilized. Comparators 150 through 150n compare signal S with reference voltages R1 through Rn, respective, corresponding to different percent weights of oil-in-wax for a sample and provide outputs corresponding to the comparison to decode means 155. Reference voltages R1 through Rn are also provided to a plurality of electronic single pole, single throw switch means 160 through 160n, respectively. Each switch means of the plurality of switch means 160 through 160n is responsive to a control signal from decode means 155 to pass or block the reference voltage it receives. The outputs of switch means 160 through 160n are commonly connected to record and display means 140.

In operation, decode means 155 activates one of the switch means of switch means 160 through 160n in response to the signals from comparators 150 through 150n resulting from the comparison of signal S with reference voltages R1 through Rn. The switch so activated provides the reference voltage it receives as signal W to record and display means 140.

Referring back to FIG. 1, as the belt moves the bottles of the tested wax continue on until they arrive at a take-off point which may be done manually or automatically. The matter of removing the bottles from the belt is not essential to an understanding of the invention heretofore described.

The present invention as herein before described is an automatic on-line apparatus for the determination of the oil content of wax coming from a dewaxing unit.

What is claimed is:

1. An on-line oil-in-wax monitor comprising means for periodically sampling a stream of liquid wax and oil to provide samples, means for solidifying the wax in each sample;

means for sensing the oil in each sample and providing a sensed oil signal corresponding thereto; and means for indicating the oil content of the stream in accordance with the sensed oil signal, said indicating means includes means connected to the sensing means for sampling and holding the sensed oil signal while it is a proper signal to provide a corresponding signal, oil signal means connected to the sample and hold means and receiving direct current voltages corresponding to a standard oil signal, to the ratio of the weight of the oil standard to the weight of the sample, and to the value of 100 for providing a signal W corresponding to the percent weight of oil in the oil and wax stream in accordance with the signal from the sample and hold means and the received direct current voltages and the following equation:

$$\% \text{ Oil} = (SW/SO)(WO/WW)100,$$

where SW corresponds to the held sensed oil signal, SO corresponds to a sensed oil signal representative of an oil standard sample, WO is the weight of the oil standard sample and WW is the weight of the sample, and indicator apparatus connected to said oil signal means which provides an indication of the percent weight of oil in the stream in accordance with signal W.

2. A monitor as described in claim 1 in which the sensing means uses low resolution nuclear magnetic resonance to sense the oil in each sample and provides a signal in accordance with that sensing.

3. A monitor as described in claim 2 in which the sampling means includes a circulating conveyor belt, dispensing means responsive to control signal for dispensing a predetermined quantity of the oil and wax liquid, a plurality of container means being arranged on the conveyor belt, and first control means responsive to the positioning of an empty container means in relation to the dispensing means for stopping movement of the conveyor belt and for providing the first control signal to fill the container means with the liquid wax and oil so as to provide a sample and for causing the conveyor belt to move again once the predetermined quantity of liquid wax and oil has entered the container means.

4. A monitor as described in claim 3 in which the solidfying means includes refrigeration means arranged with the conveyor belt so that the conveyor belt moves through the refrigeration means carrying each container means with the liquid wax and oil sample therein through refrigeration means.

5. A monitor as described in claim 4 in which the sensing means includes a test chamber, means for providing a second control signal to stop the movement of the conveyor belt when a container with solidified wax therein is in position to enter the chamber, and means for moving the container into the test chamber so that the sensing means will provide the sensed oil signal in accordance with the sample in the test chamber.

6. A method for the on-line determination of the oil content of a stream of liquid wax and oil which comprises the steps of periodically sampling the stream to provide samples, sensing the oil in each sample, providing a sensed oil signal in accordance with the sensing, providing a plurality of reference signals corresponding to different percent weights of oil in wax, comparing the sensed oil signal with the reference signals, selecting a reference signal representative of the percent weight of oil in the stream in accordance with the comparison, and indicating the oil content of the stream in accordance with the sensed oil signal selected reference signal.

7. A method as described in claim 6 in which the sensing step uses low resolution nuclear magnetic resonance to sense the oil in each sample.

* * * * *